US00PP17670P3

(12) United States Plant Patent
Khanizadeh

(10) Patent No.: US PP17,670 P3
(45) Date of Patent: May 1, 2007

(54) STRAWBERRY PLANT NAMED 'ORLEANS'

(50) Latin Name: ***Fragaria×ananassa* Duch**
Varietal Denomination: Orleans

(75) Inventor: Shahrokh Khanizadeh, Baie D'Urfé (CA)

(73) Assignee: Her Majesty The Queen In Right of Canada

( * ) Notice: Subject to any disclaimer, the term of this patent is extended or adjusted under 35 U.S.C. 154(b) by 136 days.

(21) Appl. No.: 10/839,287

(22) Filed: May 6, 2004

(65) Prior Publication Data

US 2005/0251886 P1 Nov. 10, 2005

(51) Int. Cl.
*A01H 5/00* (2006.01)

(52) U.S. Cl. ..... Plt./208
(58) Field of Classification Search ..... Plt./208
See application file for complete search history.

(56) References Cited

U.S. PATENT DOCUMENTS

PP5,262 P * 7/1984 Voth et al. ..... Plt./208
PP8,853 P * 8/1994 Buszard et al. ..... Plt./208
PP10,460 P * 6/1998 Khanizadeh et al. ..... Plt./208
PP11,438 P * 7/2000 Jamieson et al. ..... Plt./208
2003/0009799 P1 * 1/2003 Khanizadeh ..... Plt./208

OTHER PUBLICATIONS

UPOV ROM GTITM Computer Database, GTI Jouve Retrieval Software 2005/03 Citation for 'Orleans'.*
Khanizadeh, S. et al. The Quebec Strawberry breeding program of Agriculture and AgriFood Canada at St–Jean-sur–Richelieu: past and present achievements and future objectives. Acta Horticulturae (567 vol. 1) p. 129–131 Jul. 2000.*
Khanizadeh, Shahrokh et al. L'Authentique Orleans: A new strawberry cultivar with high levels of antioxidants. Hortscience 36 (3): p. 488 Jun. 2001.*
Khanizadeh, S. et al. 'Orleans' Strawberry. Advances in Strawberry Research 2002–2003 v. 21 p. 8–11.*
Maas, J. L. et al., Ellagic Acid, an Anticarcinogen in Fruits, Especially in Strawberries: A Review, HortScience, 1991, vol. 26, No. 1, pp. 10–14.

* cited by examiner

*Primary Examiner*—Wendy Haas
(74) *Attorney, Agent, or Firm*—Paul E. White, Jr.; Manelli Denison & Selter PLLC

(57) ABSTRACT

A new and distinct June-bearing strawberry cultivar named 'Orléans' is primarily adapted to the growing conditions of Eastern Central Canada and shows resistance to soil born diseases. Its upright growing habit, its small flowers with as-long-as-broad petals, its firm light-red fruit with same-sized calyx, its fruit sweetness, long shelf life and high levels of antioxidants essentially characterize 'Orléans'.

8 Drawing Sheets

Botanical designation: *Fragaria×ananassa* Duch.
Variety denomination: 'Orleans'.

FIELD OF THE INVENTION

The present invention relates to a new and distinct June bearing strawberry cultivar designated as 'Orléans'. This cultivar belongs to the genus *Fragaria×ananassa* Duch. whose fruit are juicy, edible and usually red, and is cultivated for culinary purposes.

BACKGROUND OF THE INVENTION

The new cultivar, tested as FIO9623-55, is the progeny of a cross made in 1996 by Shahrokh Khanizadeh between 'L'Acadie' (U.S. Plant patent application Publication No. 2003/0009799) and 'Joliette' (U.S. Plant Pat. No. 10,460). 'L'Acadie' is a June bearing strawberry cultivar (*Fragaria×ananassa* Duch) bred for Eastern Central Canada and more specifically for Quebec growing conditions. 'L'Acadie' is noted for large, firm fruit, moderate resistance to leaf diseases, partial resistance to red stele (*Phytophthora fragariae* Hickman), and keeping quality of several days after picking or maturity in the field. 'Joliette' has high yields of large, moderately firm fruit and is resistant to leaf spot (*Mycosphaerella fragariae* Tul.) and to six North American eastern (NAE) races of red stele (*Phytophthora fragariae* Hickman).

The 'Orléans' strawberry was asexually propagated by runners at the Agriculture and Agri-Food Canada sub-station in L'Acadie, Québec and extensively tested at the same location (where it has been tested since 1997). It was reselected by Les Fraises de L'île d'Orléans Inc. in St Laurent, Île d'Orléans, Québec, Canada in 1999. The new variety was then further evaluated from 1999 to 2001 in controlled semi-commercial sites by our private partners, Meiosis Ltd (Kent, UK). It is presently evaluated in other provinces of Canada, in the United States, and in Europe. Clones of the claimed plant are identical to the original plant. 'Orléans' is now an established and stable cultivar.

BRIEF SUMMARY OF THE INVENTION

'Orléans' is primarily adapted to the climate and growing conditions of Eastern Central Canada and more specifically for I'Île d'Orléans, Québec. It can tolerate low winter temperatures and shows resistance to soil born diseases. Its upright growing habit, its small flowers with as-long-as-broad petals, its firm light-red fruit with same-sized calyx and its fruit sweetness essentially characterize 'Orléans', as compared to 'Kent', 'L'Acadie' and 'Joliette'. 'Orléans' out-yields 'Kent' (unpatented) and produces larger fruits that ripen 4–5 days after 'Kent' fruits. 'Orléans' also continues to produce fruits 4–5 days after 'Kent', therefore it is considered as a mid-season late cultivar. 'Orléans' has a much longer shelf life than varieties like 'Chambly' (U.S. Plant Pat. No. 8,853), 'Kent', 'Annapolis' (unpatented) and 'Saint-Pierre' (unpatented) and shows higher levels of antioxidants (Gallic acid, Protocatecuic acid, Catechin, P-hydroxybenzoic acid, Epicatechin, and Ellagic acid) than 'Kent'.

BRIEF DESCRIPTION OF THE DRAWINGS

The accompanying color photographs show typical specimens of the new variety at various stages of development as nearly true as it is possible to make in color reproductions.

DETAILED BOTANICAL DESCRIPTION

Figure 1:
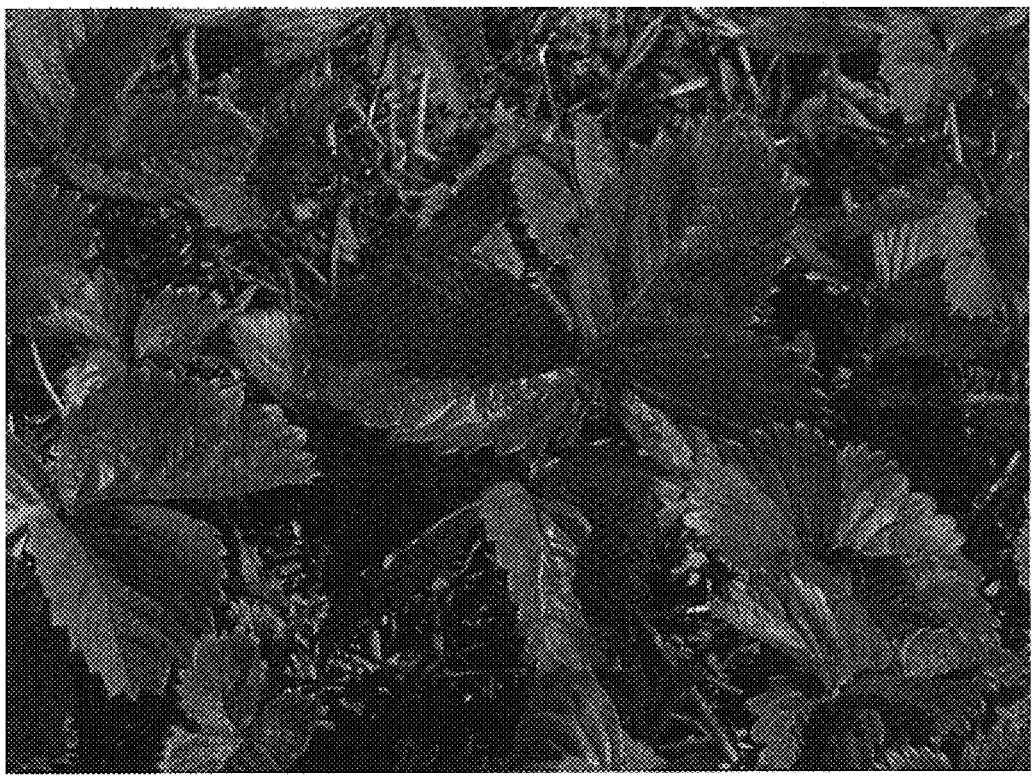
FIG. 1 shows typical 'Orléans' field plants.
Figure 2:
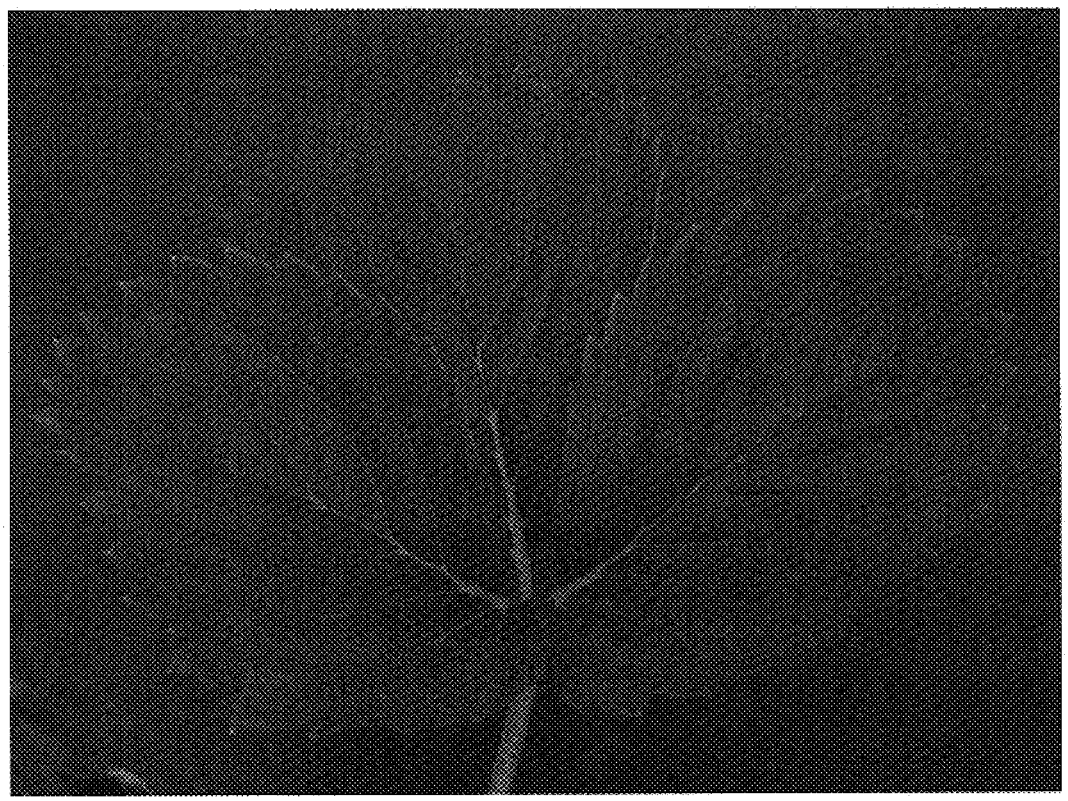
FIG. 2 shows a close-up view of a typical mature trifoliate of 'Orléans'.
Figure 3:
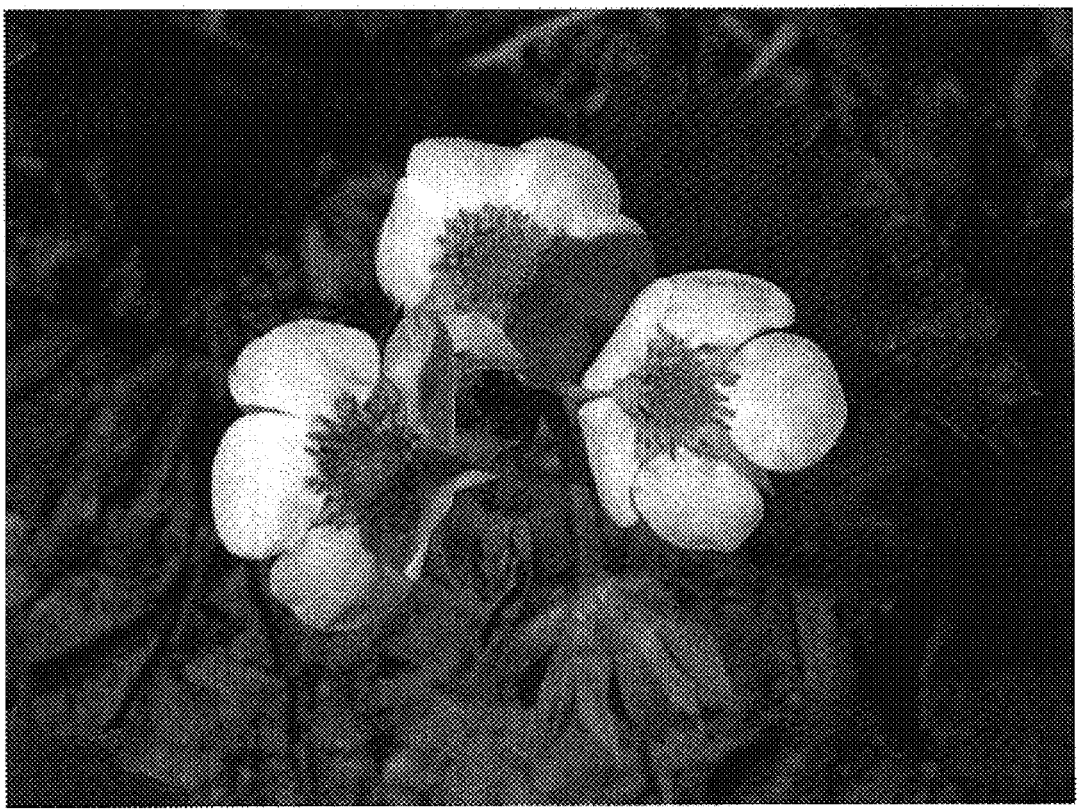
FIG. 3 shows a close-up view of typical 'Orléans' inflorescences.
Figure 4:
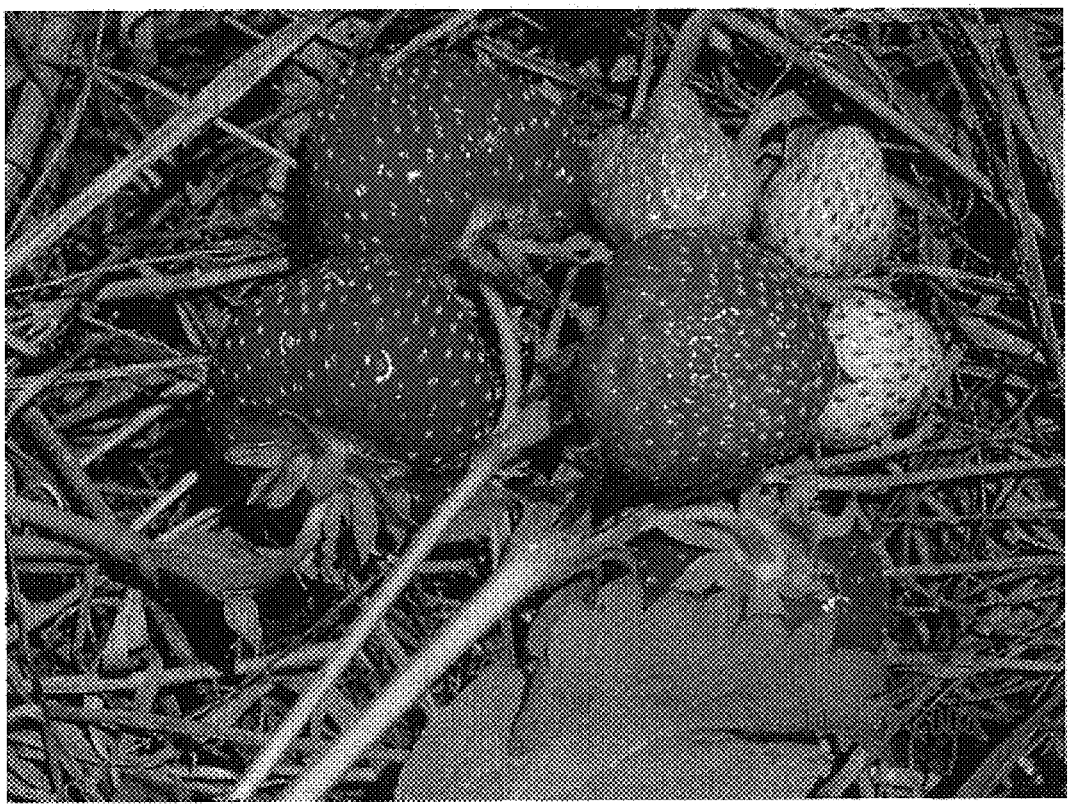
FIG. 4 shows a close-up view of typical mature and immature 'Orléans' field fruits, taken on Jul. 14, 2003.
Figure 5:
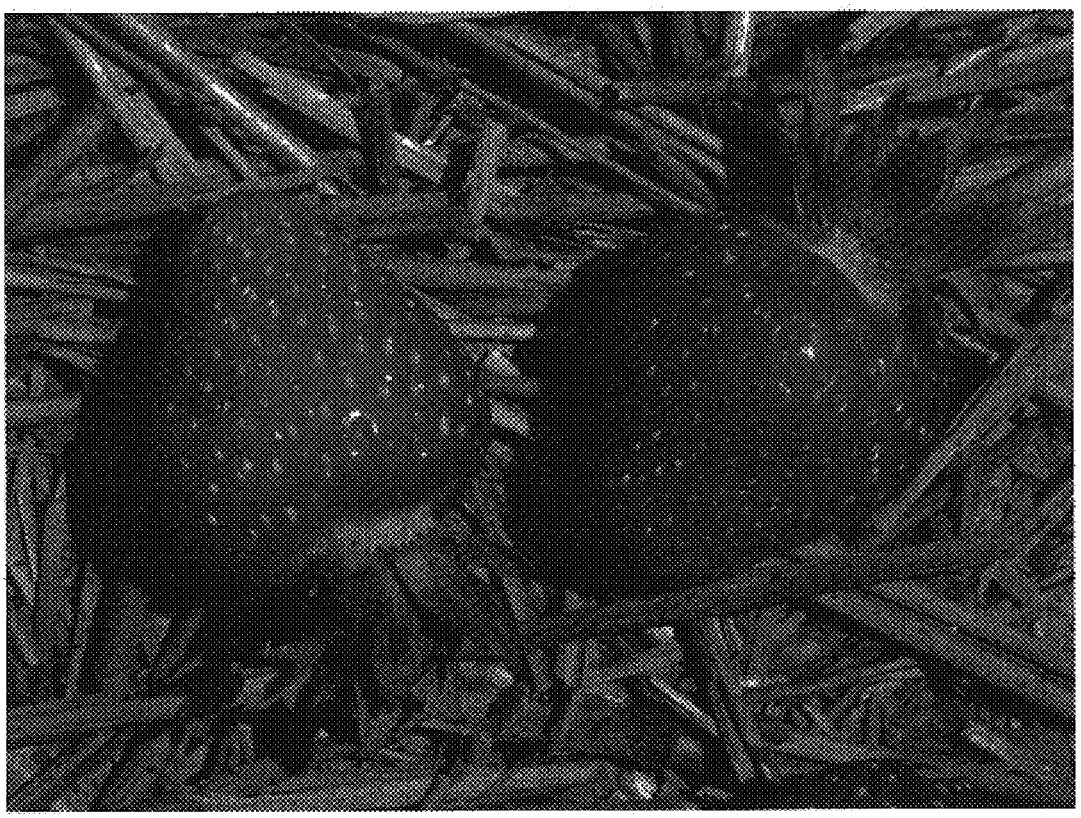
FIG. 5 shows a close-up view of 'Orléans' fruits.
Figure 6:
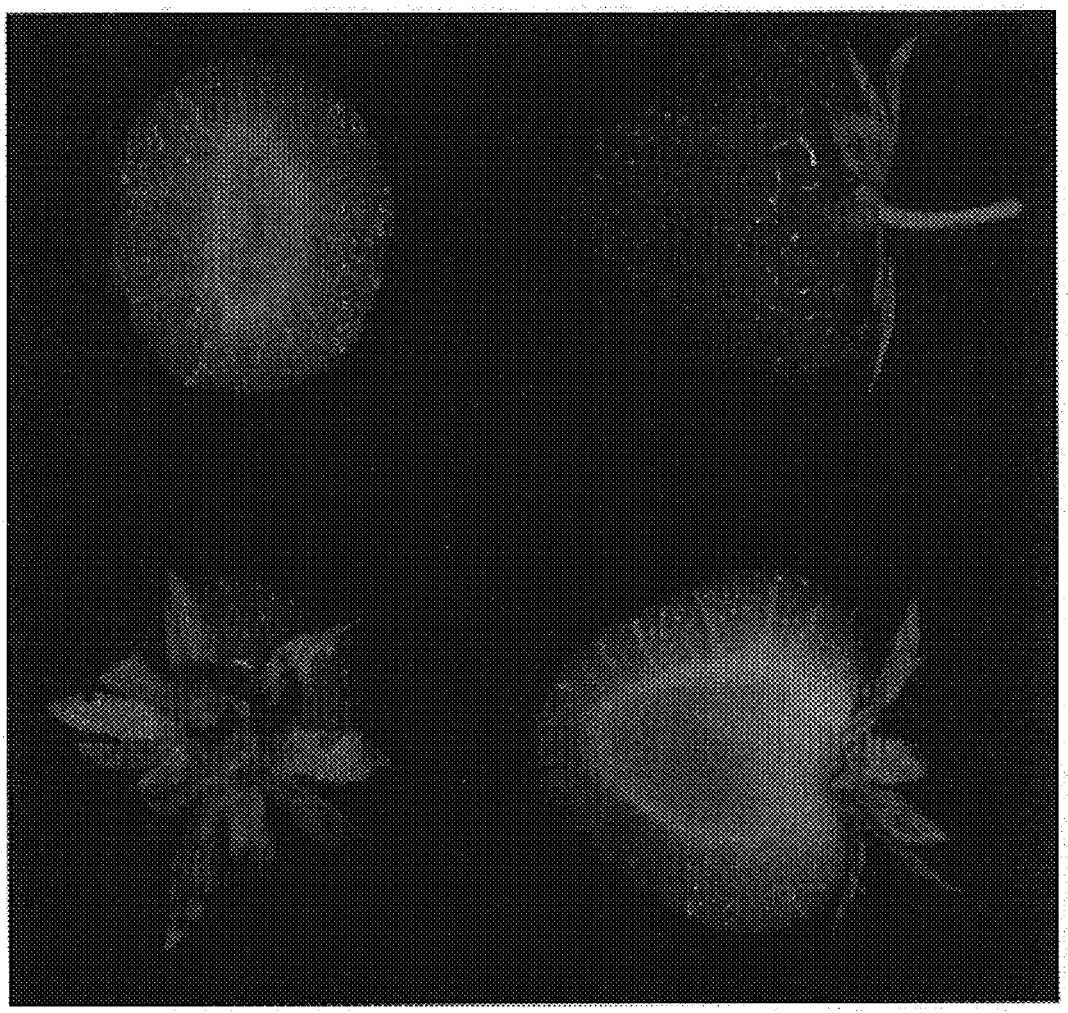
FIG. 6 shows typical internal and external fruit characteristics of 'Orléans'.
Figure 7:
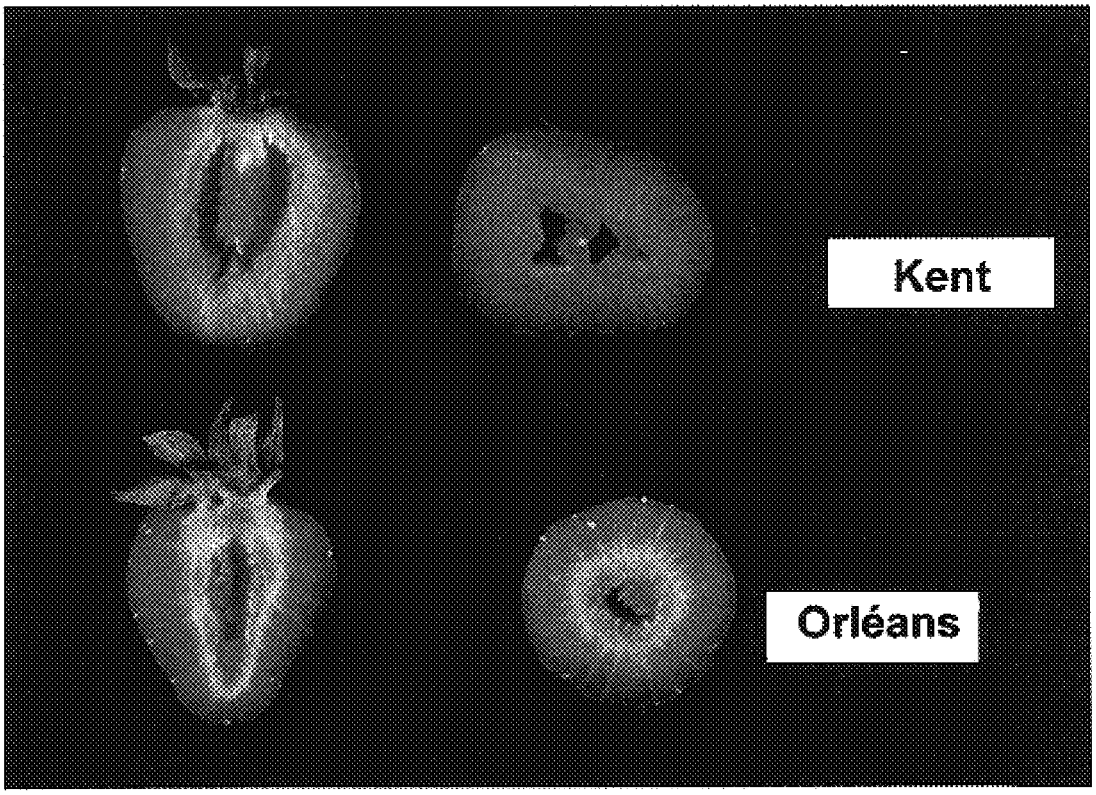
FIG. 7 shows a comparison of internal fruit characteristics between 'Orléans' and 'Kent'.
Figure 8:
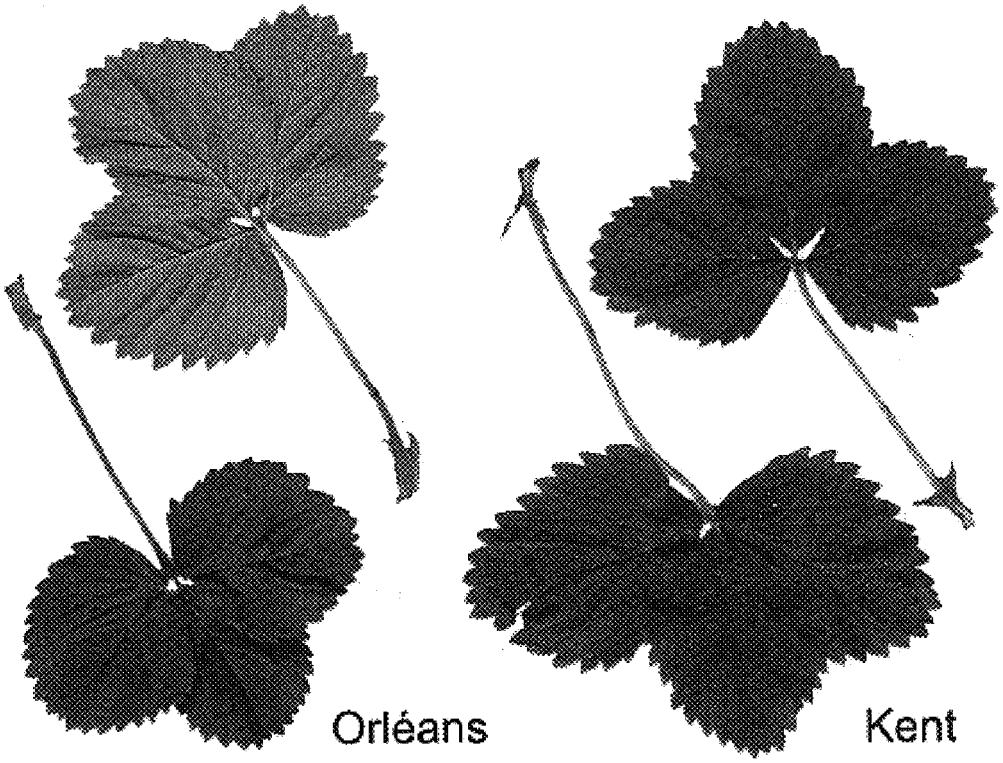
FIG. 8 shows a comparison of trifoliates between 'Orléans' and 'Kent'.

'Orléans' is a June bearing strawberry cultivar (*Fragaria*× *ananassa* Duch.), resulting from a cross between 'L'Acadie' and 'Joliette' (U.S. Plant Pat. No. 10,460). 'Orléans' has high yields of very large, firm, light-red colored fruit and performs much longer storage life than the standard variety Kent, used by many growers. It also shows higher levels of antioxidants (Gallic acid, Protocatecuic acid, Catechin, P-hydroxybenzoic acid, Epicatechin, and Ellagic acid) than 'Kent', which makes it ideal for growers who need to store the fruits for several days or ship them to other provinces for marketing.

The name 'Orléns' refers to a region east of Quebec City. This area is still recognized today as the capital for strawberry production in Quebec. L'Île d'Orléans, which was once referred to as "I'Île nourriciére" is the oldest seigneury of New France and has since then remained known as a horticultural growing region.

Plants of 'Orléans' are vigorous, have an upright growing habit and produce 3 to 4 inflorescences per crown. They can tolerate winter temperatures below −30° C. (with 10 cm straw mulch cover), they perform very well on fumigated or non-fumigated soils and show resistance to soil born diseases.

Plant characteristics

Plant:

*Overall size.*—Medium.

*Height.*—25 cm.

*Diameter.*—19 cm.

*Habit.*—Upright.

*Density* (*of individual plants in hill culture or plants/m*$^2$ *for matted rows*).—Dense.

*Low temperature tolerance.*—Typical: below −30° C.; Observed: −30° C. (January 1997).

Stolon characteristics

Stolon:

*Number.*—Typical: 4 to 6; Observed: 6.8 (Average of 10 plants).

*Anthocyanin coloration.*—From faded RHS181A to RHS 184A on the entire surface.

*Length.*—108 cm (Average of 10 plants).

*Diameter.*—2.7 mm (Average of 10 plants).

*Pubescence.*—Medium to dense.

'Orléns' fruits, fruit production and fruit quality characteristics.

TABLE 1

Yield distribution (g.m$^{-1}$ of row), total yield, fruit weight, ripening season, index of crop concentration and earliness of 'Orléans' as compared to other genotypes

| | Data collected in L'Acadie site (Québec) Harvest- Yield (g.m$^{-1}$) | | | | | |
|---|---|---|---|---|---|---|
| Genotypes | 1[z] | 2 | 3 | 4 | 5 | 6 |
| Orléans | 0.0 | 0.0 | 755.5 | 1733.1 | 2131.7 | 2549.1 |
| Annapolis | 1323.4 | 2439.8 | 3253.9 | 1480.6 | 771.4 | 1368.5 |
| Chambly | 3137.7 | 1342.8 | 1069.7 | 563.7 | 0.0 | 0.0 |
| Honeoye (Unpatented) | 1568.6 | 1800.0 | 2530.3 | 1884.9 | 641.3 | 256.6 |
| Kent | 324.6 | 1246.2 | 1593.7 | 1270.5 | 1587.8 | 985.7 |
| Mira (U.S. Plant Pat. No. 11,438) | 332.2 | 821.8 | 2287.0 | 2316.9 | 1729.5 | 1784.6 |
| St-Pierre | 0.0 | 0.0 | 0.0 | 1643.7 | 1506.9 | 0.0 |

| Genotypes | 7 | 8 | 9 | 10 | Total yield (g.m$^{-1}$) |
|---|---|---|---|---|---|
| Orléans | 2075.4 | 1415.8 | 1399.4 | 289.5 | 12349.5 |
| Annapolis | 0.0 | 40.6 | 0.0 | 0.0 | 10678.2 |
| Chambly | 0.0 | 0.0 | 0.0 | 0.0 | 6113.9 |
| Honeoye (Unpatented) | 203.7 | 13.4 | 0.0 | 0.0 | 8898.8 |
| Kent | 646.9 | 304.5 | 240.1 | 203.6 | 8403.6 |
| Mira (U.S. Plant Pat. No. 11,438) | 1074.3 | 25.7 | 0.0 | 0.0 | 10372.0 |
| St-Pierre | 3326.4 | 1371.1 | 0.0 | 687.6 | 8535.7 |

| | Data collected in L'Acadie site (Québec) | |
|---|---|---|
| Genotypes | Wt./fruit (g)[y] | Ripening season[x] |
| Orléans | 12.6 | M |
| Annapolis | 10.7 | E |
| Chambly | 10.4 | EM |
| Honeoye | 9.5 | EM |
| Kent | 8.2 | EM |
| Mira | 10.7 | LM |
| St-Pierre | 9.9 | L |

[z]Number of times fruits were harvested during the season $LSD_{0.05}$

[y]Average over 4 years (1995–1998), minimum of 4 replications per year, data from the l'Acadie site.

[x]L = Late, LM = Late-Midseason, M = Midseason, EM = Early-Midseason, E = Early.

TABLE 2

Firmness, flavour, skin color, leaf disease susceptibility and shelf life of "Orléans, as compared to other genotypes[2]
Data collected in L'Ile d'Orléans (St Laurent, Québec) site.

| Genotypes | Firmness[y] | Flavor[y] | Skin color[y] | Leaf disease[y] susceptibility | Shelf life[x] |
|---|---|---|---|---|---|
| Orléans | 4.4 | 4.5 | 2.3 | 4.8 | 5.0 |
| Annapolis | 2.9 | 2.0 | 2.0 | 3.4 | 2.0 |
| Honeoye | 3.0 | 2.9 | 4.1 | 3.9 | 1.5 |
| Kent | 2.8 | 4.0 | 3.4 | 2.3 | 0.5 |
| Mira | 2.7 | 1.8 | 2.0 | 3.4 | 1.0 |
| St-Pierre | 3.3 | 3.4 | 2.2 | 3.0 | 2.5 |

[2]Averaged over 3 years (1999–2001), minimum of four replications per year.
[y]Data were transformed to arcsin prior to analysis of variance (SAS Institute, 1988).
Firmness: 1 = very soft, 5 = very firm
Flavor: 1 = poor, 5 = excellent
Skin color: 1 = very pale, 5 = dark red
Leaf disease susceptiblity: 1 = very susceptible, 5 = resistant
[x]Number of days at room temperature for which the fruits were more than 95% marketable.

Fruit:

*Ratio of length/maximum width.*—As long as broad to slightly longer than broad.
*Size.*—Medium to large.
*Length of primary fruits.*—3.2 cm (Average of 10 fruits).
*Width of primary fruits.*—3.2 cm (Average of 10 fruits).
*Length of secondary fruits.*—2.7 cm (Average of 10 fruits).
*Width of secondary fruits.*—2.8 cm (Average of 10 fruits).
*Weight of primary fruit.*—13.26 g (Average of 25 fruits).
*Weight of secondary fruit.*—7.82 g (Average of 25 fruits).
*Predominant shape.*—Conical (slightly globose).
*Difference in shape between primary and secondary fruits.*—Non to very slight.
*Color of fruit stem.*—143C.
*Band without achenes.*—Narrow.
*Unevenness of surface.*—Weak.
*Skin color.*—RHS 45A.
*Evenness of color.*—Slightly uneven.
*Glossiness.*—Strong.
*Insertion of achenes.*—Below surface.
*Color of achenes.*—RHS 150C.
*Insertion of calyx.*—Level.
*Attitude of the calyx segments.*—Clasping to reflexed.
*Size of the calyx in relation to fruit diameter.*—Same size.
*Calyx depth of secondary fruits.*—Typical: 0.5 to 1.1 mm; Observed 0.6 mm (Average of 10 fruits).
*Calyx diameter.*—Typical: 2.2 to 2.8 cm; Observed 1.8 to 2.1 mm (Average of 10 fruits).
*Adherence of the calyx.*—Strong.
*Attitude of sepals.*—Reflexed. Firmness of flesh, when fully ripe (measured manually by a sensory panel; where 1=very soft and 5=very firm). Typical: 2.8 (cultivar standard: Kent); Observed: 4.4.
*Color of flesh.*—RHS 34A.
*Evenness of color of flesh.*—Even.
*Sweetness (% Brix).*—8.3 to 11.0%.
*Texture when tested.*—Fine.
*Acidity.*—0.68%.
*Time of flowering (50% of plants at first flower).*—Medium.
*Date of first bloom.*—June 3rd (Average of 4 years).
*Date of full bloom.*—June 7th (Average of 4 years).
*Harvest maturity (50% of plants with ripe fruits).*—Mid-season.
*Date of first harvest.*—June 27th (Average of 4 years).
*Type of bearing.*—Not everbearing.

'Orléans' differs from its parents ('Joliette' and 'L'Acadie') in terms of fruit shape, calyx and fruit color. As stated earlier, 'Orléans' fruit is globose-conic with reflexed sepals rested on a white short neck with very light glossy red color, whereas 'Joliette' fruit change from globose to short-wedge shape during the harvest. 'Joliette' skin is reddish and its sepals are not reflexed. 'L'Acadie' fruits are shiny pale red, with a necked-conic predominant shape and the calyces are semi-reflexed.

Chemical analysis of the 'Orléans' fruits reveal high levels of free epicatechin and ellagic acid and above the average to very high levels of bound catechin, epicatechin and ellagic acid. Free antioxidants are immediately available to the plant and therefore help its resistance against diseases or other external stresses. They also act to extend shelf life and enhance quality preservation by delaying senescence created by oxidative degradation. Bound antioxidants, which are measured after hydrolyzing samples, are chemicals that can provide a health benefit after ingestion. For example, ellagic acid and catechin have been shown to have anti-carcinogenic and anti-inflammatory properties (Ellagic acid, an anticarcinogen in fruits, especially in strawberries: a review, Mass et al., HortScience 26:10–14, 1991).

The 'Orléans' fruit has a long shelf life, over 5 days at 4° C. (Table 2) and 3–4 days at room temperature.

Foliage characteristics

Leaf:

*Length.*—7.1 cm (Average of 10 leaves).
*Width.*—6.8 cm (Average of 10 leaves).
*Green color of upper side.*—138A.
*Green color of lower side.*—138B.
*Profile (angle terminal leaflet subtends to the petiole).*—Slightly concave.
*Blistering (interveinal blisters).*—Weak.
*Number of leaflets.*—Three.
*Color of leaflet stems.*—143C (white in bloom).
*Leaflet number of serrations.*—24–30.

Terminal leaflet:

*Profile.*—Flat to slightly cupped.
*Length/width ratio.*—As long as broad.
*Shape of base.*—Obtuse to rounded.
*Shape of teeth.*—Acute to obtuse.

Petiole:

*Length.*—10–15 cm.
*Diameter.*—2.7 mm (Average of 10 petioles).
*Pubescence.*—Medium.
*Color.*—143C (before bloom).
*Pose of hairs.*—Upwards to outwards.

Flowers and Inflorescences characteristics.

Inflorescence:

*Position relative to foliage.*—Below to level with.
*Attitude of fruit trusses (at first picking).*—Semi erect.
*Length of fruiting trusses.*—9 to 13 cm.

Flowers:

*Size.*—Small.

*Diameter of secondary flowers.*—1.7 to 1.9 cm.

*Depth of secondary flowers.*—2 mm.

*Calyx diameter of secondary flowers.*—1.8 to 2.1 cm.

*Diameter of calyx relative to corolla.*—Larger.

*Diameter of inner calyx relative to outer on secondary flowers.*—Same size to larger.

*Spacing of petals on secondary flowers with 5 to 6 petals.*—Touching to touching-overlapping.

*Petal length/width ratio on secondary flowers.*—As long as broad.

*Length of petals on secondary flowers.*—0.7 cm.

*Width of petals on secondary flowers.*—0.7 cm.

*Shape of petals on secondary flowers.*—Mainly circular.

*Margin shape of petals on secondary flowers.*—Circular.

*Apex shape of petals on secondary flowers.*—Rounded.

*Base shape of petals on secondary flowers.*—Broad obtuse to almost circular.

*Color of petals.*—Pure white on both upper and lower surfaces (no corresponding RHS color).

*Number of sepals.*—12.

*Length of sepals on secondary flowers.*—0.5 to 0.7 mm.

*Width of sepals on secondary flowers.*—2.0 to 3 mm.

*Overall shape of sepals on secondary flowers.*—Linear.

*Margin shape of sepals on secondary flowers.*—Elongated triangle.

*Base shape of sepals on secondary flowers.*—Straight, not tapered.

*Apex shape of sepals on secondary flowers.*—Acute.

*Color of upper surface of sepals.*—143A.

*Color of lower surface of sepals.*—143C.

*Length of flower buds.*—7 mm.

*Diameter of flower buds.*—7 mm.

*Color of flower buds.*—Entirely white (no corresponding RHS color).

*Size of stamens relative to pistils.*—Longer.

*Color of anthers.*—9C.

*Color of stamen.*—3D.

*Color of pistil.*—3D.

*Color of pollen.*—9C.

Some symptoms of powdery mildew were noted on 'Orléans' plants, as observations began in 1996 during prolonged high humidity. However, 'Orléans' plants are less susceptible to mildew than 'Kent'. 'Orléans' plants are resistant to leaf scorch (*Diplocarpon earlina* Ell. & Ev.), leaf blight (*Dendrophoma obscurans* Ell. & Ev.) and leaf spot (*Mycosphaerella fragariae* (Tul.) Lindau), as compared to 'Kent' control plants that are very susceptible to all these leaf diseases. 'Orléans' is resistant to soil-born diseases.

'Orléans' plants are more vigorous than 'Chandler' (U.S. Plant Pat. No. 5,262) in both fumigated and non-fumigated soils. 'Orléans' is recommended for Eastern Central Canada, especially in areas where the climate is similar to that in the strawberry production areas of Québec, for example, I'Acadie (35km South East of Montreal Island, Québec, lat. 45° N and 46 m elevation). The climate at L'Acadie, where 'Orléans' has been extensively tested, is characterized by extreme low temperatures in winter (<−25° C.); cool, wet, humid conditions in spring; and warm, humid conditions in summer (25–35° C., 70% RH). It has a clay loam soil with moderate to low drainage and little snow cover during the winter.

What is claimed is:

1. A new and distinct strawberry plant named 'Orléans' as described and illustrated herein.

* * * * *